(12) United States Patent
Olcott et al.

(10) Patent No.: US 9,435,898 B2
(45) Date of Patent: Sep. 6, 2016

(54) DEDICATED CARDIAC PET

(71) Applicant: The Board of Trustees of the Leland Stanford Junior University, Palo Alto, CA (US)

(72) Inventors: Peter D. Olcott, Los Gatos, CA (US); Craig Steven Levin, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 15 days.

(21) Appl. No.: 14/358,832

(22) PCT Filed: Nov. 16, 2012

(86) PCT No.: PCT/US2012/065465
§ 371 (c)(1),
(2) Date: May 16, 2014

(87) PCT Pub. No.: WO2013/074894
PCT Pub. Date: May 23, 2013

(65) Prior Publication Data
US 2014/0306118 A1 Oct. 16, 2014

Related U.S. Application Data

(60) Provisional application No. 61/561,168, filed on Nov. 17, 2011.

(51) Int. Cl.
*G01T 1/202* (2006.01)
*G01T 1/20* (2006.01)
(Continued)

(52) U.S. Cl.
CPC .............. *G01T 1/202* (2013.01); *A61B 6/037* (2013.01); *A61B 6/4233* (2013.01); *A61B 6/508* (2013.01); *G01T 1/164* (2013.01); *G01T 1/2018* (2013.01)

(58) Field of Classification Search
CPC ..... G01T 1/1644; G01T 1/202; G01T 1/1642
USPC .......... 250/366, 370.11, 361 R, 363.01, 368, 250/369
See application file for complete search history.

(56) References Cited

U.S. PATENT DOCUMENTS 4,299,066 A * 11/1981 Thompson .................... 52/81.6
5,185,778 A 2/1993 Magram
(Continued)

OTHER PUBLICATIONS

Massoth, Shielding Evaluation for Mobile PET/CT Facilites, Jul. 27, 2007.*
(Continued)

*Primary Examiner* — David Porta
*Assistant Examiner* — Djura Malevic
(74) *Attorney, Agent, or Firm* — Beyer Law Group LLP

(57) ABSTRACT

A detector is provided. A plurality of scintillation crystals is provided, where each scintillation crystal has a width, and wherein a first plurality of scintillation crystals is placed adjacent to each other so that first surfaces of the first plurality of scintillation crystals form a first rectangular surface. A reflective coating is formed over the first rectangular surface with an open region grid pattern, wherein each open region forms a space wherein each space has a width equal to the width of a scintillation crystal of the plurality of crystals. A plurality of photodetectors is provided, wherein each photodetector is placed over a space, wherein the photodetector has a width greater than the width of the space over which the photodetector is placed. At least one electronic readout is electrically connected to the plurality of photodetectors.

14 Claims, 10 Drawing Sheets

(51) Int. Cl.
*A61B 6/03* (2006.01)
*A61B 6/00* (2006.01)
*G01T 1/164* (2006.01)

(56) References Cited

U.S. PATENT DOCUMENTS

| | | | |
|---|---|---|---|
| 5,378,894 A * | 1/1995 | Akai | 250/368 |
| 5,420,429 A * | 5/1995 | Eberhard et al. | 250/367 |
| 6,553,092 B1 * | 4/2003 | Mattson et al. | 378/19 |
| 6,808,308 B2 | 10/2004 | Thompson | |
| 6,909,097 B2 * | 6/2005 | Schreiner et al. | 250/366 |
| 7,157,014 B1 * | 1/2007 | Andreaco et al. | 216/24 |
| 7,161,156 B2 * | 1/2007 | Wirth | 250/370.11 |
| 7,418,802 B2 * | 9/2008 | Sarine et al. | 52/79.5 |
| 7,511,292 B2 * | 3/2009 | Baudro | 250/515.1 |
| 7,665,249 B2 * | 2/2010 | Zeik et al. | 52/79.1 |
| 7,742,562 B2 * | 6/2010 | Weber | A61B 6/0457 378/209 |
| 7,968,853 B2 * | 6/2011 | Altman et al. | 250/370.11 |
| 8,481,952 B2 * | 7/2013 | Menge et al. | 250/368 |
| 8,547,710 B2 * | 10/2013 | Ruehl et al. | 361/816 |
| 8,586,933 B2 * | 11/2013 | Levene et al. | 250/366 |
| 8,800,215 B2 * | 8/2014 | Yoder | 52/79.1 |
| 2002/0190214 A1 * | 12/2002 | Wieczorek et al. | 250/367 |
| 2007/0007460 A1 * | 1/2007 | Hochstetler et al. | 250/370.11 |
| 2007/0007461 A1 * | 1/2007 | Yanada et al. | 250/370.11 |
| 2007/0262261 A1 * | 11/2007 | Liang | 250/368 |
| 2008/0276554 A1 * | 11/2008 | Sheetz | 52/239 |
| 2009/0065700 A1 * | 3/2009 | Menge et al. | 250/368 |
| 2009/0110152 A1 | 4/2009 | Manzke | |
| 2009/0134334 A1 * | 5/2009 | Nelson | 250/361 R |
| 2009/0224164 A1 * | 9/2009 | Lewellen et al. | 250/370.11 |
| 2009/0236534 A1 * | 9/2009 | Selfe et al. | 250/370.11 |
| 2009/0261262 A1 * | 10/2009 | Hunt | 250/370.11 |
| 2010/0012846 A1 * | 1/2010 | Wang | 250/362 |
| 2010/0108896 A1 | 5/2010 | Surti | |
| 2010/0127178 A1 * | 5/2010 | Laurence et al. | 250/363.04 |
| 2010/0127180 A1 * | 5/2010 | Lifshitz et al. | 250/367 |
| 2010/0148074 A1 * | 6/2010 | Menge et al. | 250/362 |
| 2010/0155610 A1 * | 6/2010 | Menge et al. | 250/368 |
| 2010/0173445 A1 | 7/2010 | Danzer | |
| 2010/0193713 A1 * | 8/2010 | Bichay | 250/517.1 |
| 2010/0270462 A1 * | 10/2010 | Nelson et al. | 250/252.1 |
| 2011/0017916 A1 | 1/2011 | Schulz | |
| 2012/0324648 A1 * | 12/2012 | Amano | A61B 6/037 5/601 |
| 2013/0014452 A1 * | 1/2013 | Hill et al. | 52/79.1 |
| 2013/0036702 A1 * | 2/2013 | Pacetti et al. | 52/653.2 |
| 2013/0111825 A1 * | 5/2013 | Lefkus et al. | 52/79.1 |

OTHER PUBLICATIONS

International Search Report dated Mar. 29, 2013 from International Patent Application No. PCT/US2012/065465.
Written Opinion dated Mar. 29, 2013 from International Patent Application No. PCT/US2012/065465.

* cited by examiner

DEDICATED CARDIAC PET

CROSS REFERENCE TO RELATED APPLICATIONS

This application claims priority under 35 U.S.C. §119 from U.S. Provisional Patent Application No. 61/561,168, filed Nov. 17, 2011, entitled FOCAL DUAL PANEL SCANNER, which is incorporated herein by reference for all purposes.

FIELD OF THE INVENTION

A field of the invention is imaging. Example applications of the invention include, but are not limited to, nuclear imaging, nuclear medicine, clinical molecular imaging, or small animal molecular imaging.

BACKGROUND OF THE INVENTION

Positron emission tomography is a diagnostic imaging modality that is used to non-invasively measure the biodistribution of a radioactive tracer. In positron emission tomography, a positron emitting bare radioactive isotope or an isotope that has been attached to a chemical molecule, is injected into a patient or animal. A positron is emitted by the radioactive isotope and annihilates with an electron producing two photons in opposite directions. Each of the photons has approximately 511 keV of energy, corresponding to the mass of the positron and electron. These two annihilation photons escape the patient and interact in a scanner that is positioned around the patient.

A scanner is made of arrays of high energy photon detectors that convert interactions in the detector into electrical signals that are processed on a computer. An example of a high energy photon detector is a scintillation crystal that is connected to an optical photodetector such as a photomultiplier tube or solid state photomultiplier. The photon is classified as high energy because the photon has an energy that 511 keV, or kila electron volt, which is much larger than optical photons that have energies in the 2-5 eV range. The annihilation photon can interact in the high-Z dense scintillation crystal, which in turn emits blue photons that bounce inside of the scintillation crystal. The blue optical photons propagate inside the crystal and are absorbed by a photodetector converting the light into an electrical signal. The electrical signal is then processed by analog and digital electronic circuits and is recorded as an event. The data acquisition electronics process the signal and records the time, location of the crystal or crystals that absorbed the high energy photon and any secondary interaction processes, and the energy of sum energy of the incoming high energy annihilation photon to storage. In positron emission tomography, the two photons are paired by their timestamps to produce a line-of-response (LOR) of the interaction. These LORs are processed by image reconstruction algorithms to produce 3-D images of the distribution of the radiotracer. High energy photon detector elements are placed around the object to be imaged covering a certain solid angle or angular coverage. The solid angle, or angular coverage around the object to be imaged, plus the efficiency of stopping and detecting the annihilations photons determines the sensitivity of the scanner. A scanner with a higher sensitivity will potentially have a better image quality or a shorter scan time than a scanner with a lower sensitivity. The cost of a scanner is directly related to the number of detection elements in the system. The scanning geometry is designed to optimize the sensitivity as a function of cost, size, and disposition of the object being imaged. The high energy photon detectors have depth-of-interaction capability to remove the blurring that results from photons that penetrate into the crystal. Better the depth resolving capability of the depth-of-interaction detector will result in a more uniform spatial resolution.

A time-of-flight scanner is one where the arrival time of the photons are recorded to such an extent that the annihilation location can be estimated. Because annihilation photons travel at the speed of light, the annihilation location can be estimated by the following equation: delta_x=delta_t/2*c), where delta_x is location of the annihilation measured from the center of the line, delta_t is the difference in time measured by the detectors, and c is the speed of light. Time-of-flight information can significantly improve limited angle PET by providing information that was lost.

SUMMARY OF THE INVENTION

Embodiments of the invention provide a detector. A plurality of scintillation crystals are provided, where each scintillation crystal of the plurality of scintillation crystals has a width, and wherein a first plurality of scintillation crystals of the plurality of scintillation crystals is placed adjacent to each other so that first surfaces of the first plurality of scintillation crystals form a first rectangular surface. A reflective coating is provided over the first rectangular surface with an open region grid pattern, wherein each open region forms a space wherein each space has a width equal to the width of a scintillation crystal of the plurality of crystals. A plurality of photodetectors is provided, wherein each photodetector of the plurality of photodetectors is placed over a space, wherein the photodetector has a width greater than the width of the space over which the photodetector is placed. At least one electronic readout is electrically connected to the plurality of photodetectors. In another manifestation of the invention, a self-shielded positron emission tomography (PET) scanner is provided. A dedicated PET scanner is provided. An optically transparent high energy photon shield is placed adjacent to the dedicated PET scanner. A high energy photon shield is connected to the optically transparent high energy photon shield wherein at least a third of a length the high energy photon shield has a height less than or equal to 7 feet, wherein the optically transparent high energy photon shield and the high energy photon shield surround the dedicated PET scanner with an open top.

DETAILED DESCRIPTION

Scanner

Figure 1A:
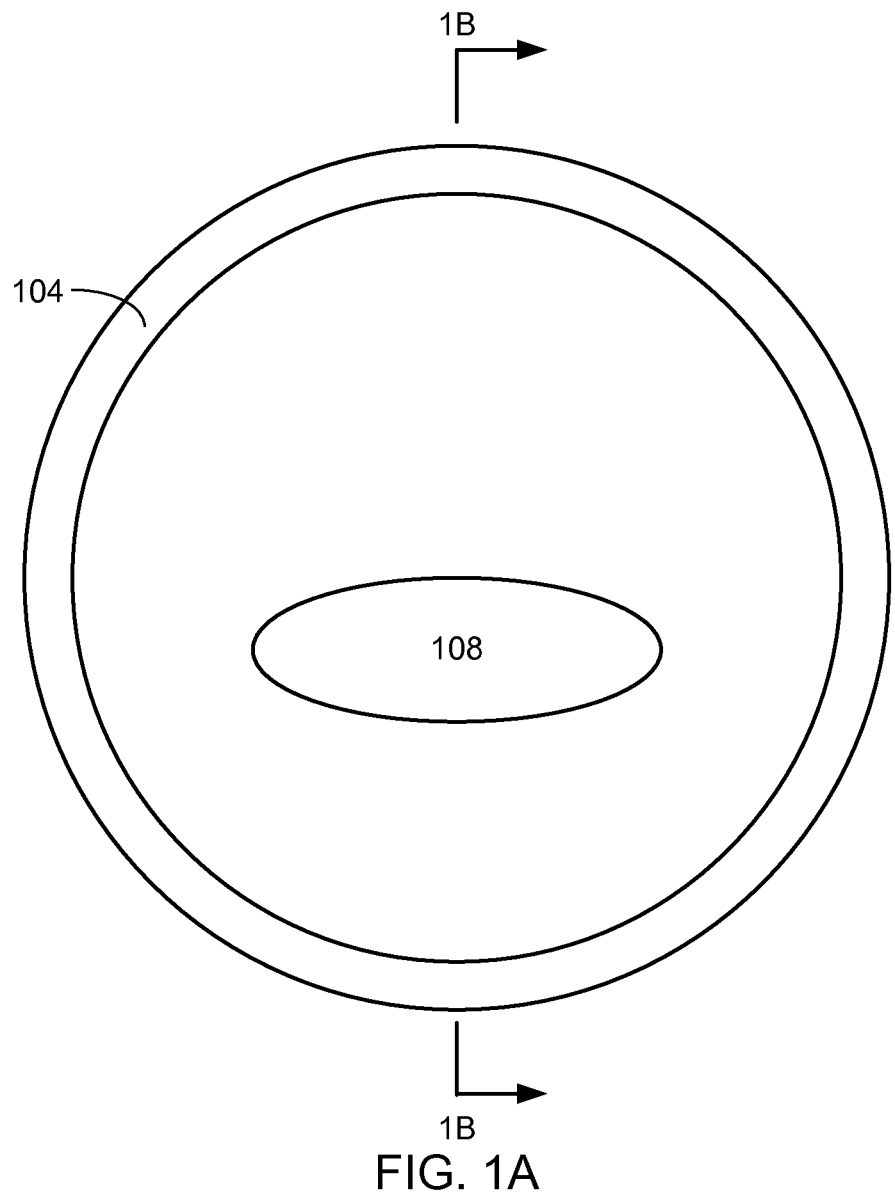
FIG. 1A is a cross sectional view of a depth-of-interaction scanner with an object, where the depth along the crystal is encoded using a special high-energy photon detector.
Figure 1B:
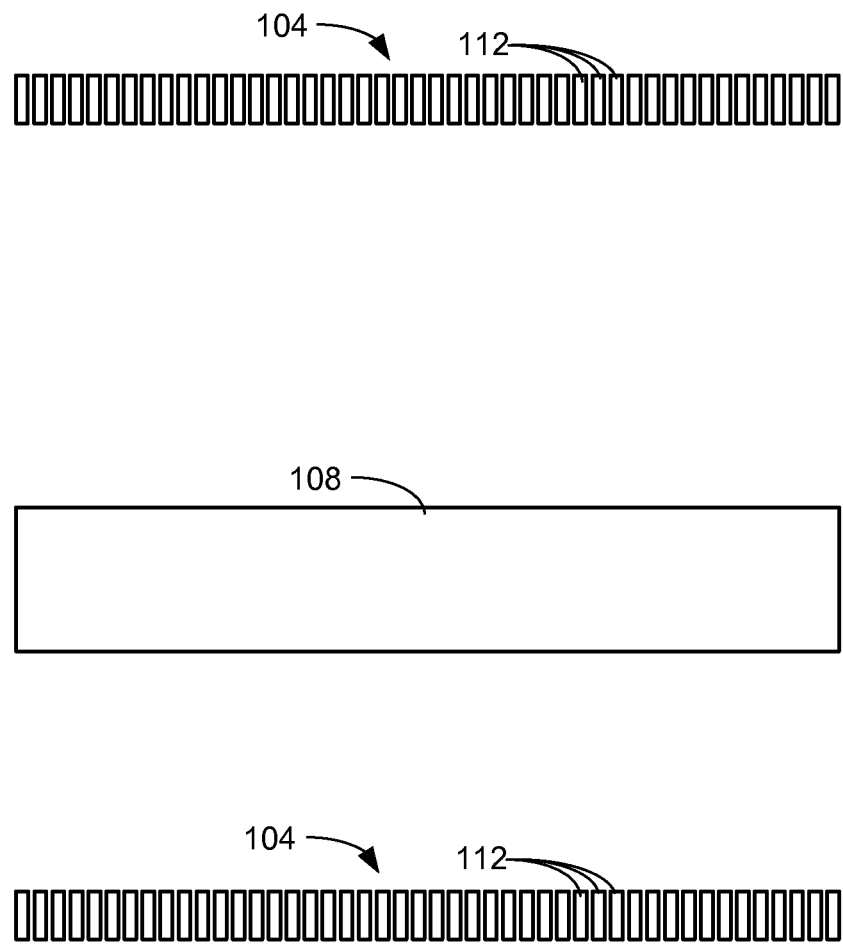
FIG. 1B is a cross sectional view of the depth-of-interaction scanner along cut line 1B that shows that the depth-of-interaction scanner is made of a plurality of individual scintillation crystals.

FIG. 1A is a cross sectional view of a depth-of-interaction scanner 104 with an object 108, where the depth along the crystal is encoded using a special high-energy photon detector. FIG. 1B is a cross sectional view of the depth-of-interaction scanner 104 along cut line 1B that shows that the depth-of-interaction scanner 104 is made of a plurality of individual scintillation crystals 112. Because the photon has significant depth of penetration in the scintillation crystal 112, significant blurring of the true line of response can occur. By recording the photon depth-of-interaction, this source of blurring is removed. Also, because the time-of-flight is important, the variance in the recorded depth in the detector also adds to the time-of-flight uncertainty. By incorporating depth-of-interaction with time-of-flight, this error can be removed.

Figure 2:
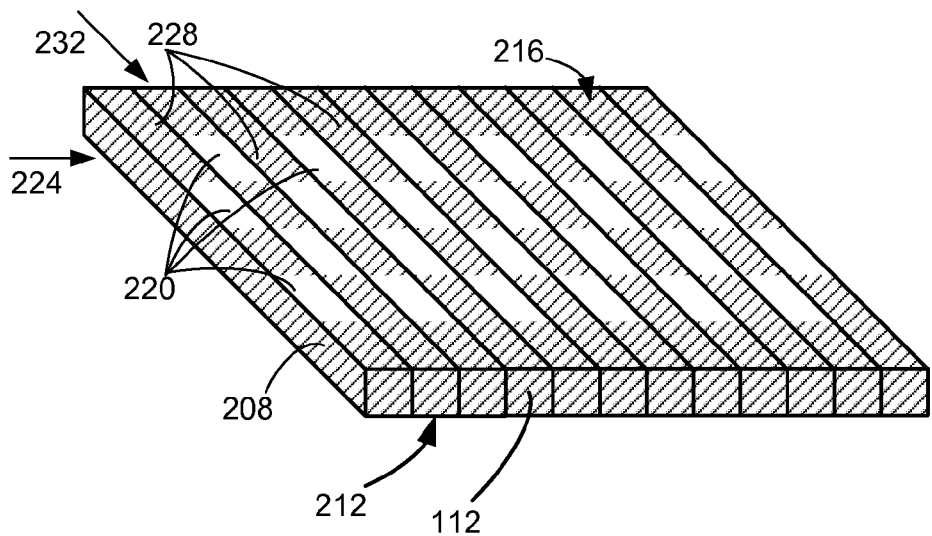
FIG. 2 is a perspective view of a row of scintillation crystals placed next to each other.

FIG. 2 is a perspective view of a row 212 of scintillation crystals 112 placed next to each other. Each scintillation crystal 112 is in the shape of a right rectangular prism. The longest dimension of each scintillation crystal 112 is the length, and the two shorter dimensions of each scintillation crystal 112 are widths. In this example, the two shorter dimensions are equal, so that an end of each scintillation crystal 112 is square. In other embodiments, the two shorter dimensions are not equal. Preferably, the length is at least 2 times longer than the widths. A reflective coating 208, shown as a shaded region, is formed over all six faces of each scintillation crystal 112. The scintillation crystals 112 are placed so that the lengths of each scintillation crystal 112 are parallel and so that a side of each scintillation crystal 112 is along a plane, so that the sides form a flat planar surface. Although all other surfaces with coatings have solid continuous reflective coating 208, a flat planar surface formed by the row 212 of scintillation crystal 112 has open regions 220, which are shown as unshaded regions, forming a reflective coating 208 with an open region grid 216. A reflective coating 208 with an open region grid 216 is defined in the specification and claims as a reflective coating 208 with at least one opening per scintillation crystal 112, where each opening has a dimension that is not greater than a width of the scintillation crystals 112, so that the openings do not extend beyond going from one side of a scintillation crystal 112 to another side of the scintillation crystal 112, as shown. In this embodiment, the open region grid 216 has two openings per scintillation crystal 112. In this embodiment, moving in a direction, as shown by arrow 224, alternating open regions 220 and coated regions 228 of the flat planar surface are encountered. Likewise, moving in a direction orthogonal to arrow 224, as shown by arrow 232, alternating open regions 220 and coated regions of the flat planar surface are encountered. In this embodiment, the open region grid 216 forms a checkerboard reflective coating, which is defined in the specification and claims has having alternating open regions 220 and coated regions 228 in two orthogonal directions.

Figure 3:
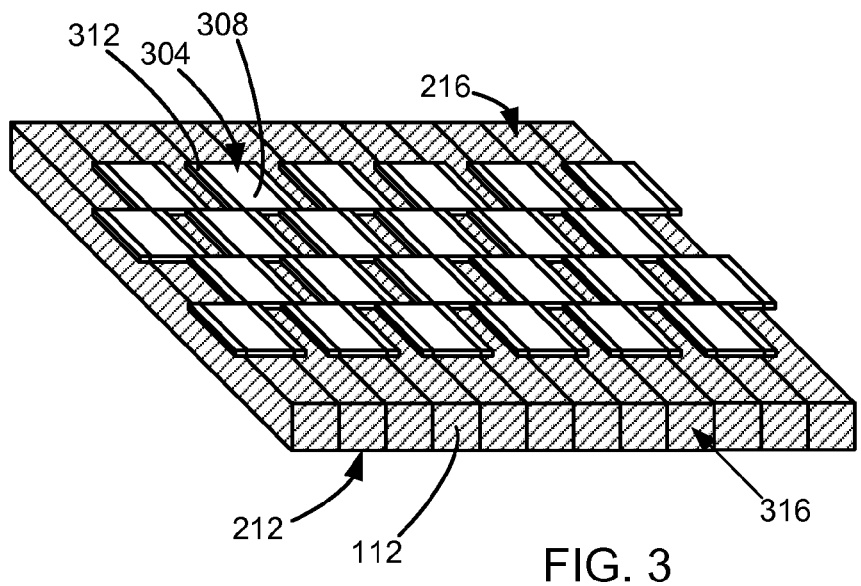
FIG. 3 is a perspective view of the row of scintillation crystals after photodetectors are placed over the openings in the open region grid.

FIG. 3 is a perspective view of the row 212 of scintillation crystals 112 after photodetectors 304 are placed over the openings in the open region grid 216. Each photodetector 304 has an active area 308, which sense photons, and a dead area 312, which does not sense photons. In the embodiment, the active area 308 of the photodetector 304 is the same size as the openings in the checkerboard. Therefore, the active area 308 of the photodetector 304 has the same dimensions as the opening, which means that a dimension of the active area 308 of the photodetector 304 is equal to a width of the scintillation crystal 112, so that the active area 308 of the photodetector 304 extends from one side of the scintillation crystal 112 to the other side of the scintillation crystal 112. Because each photodetector 304 also has a dead area 312, a dimension of the photodetector 304 must be greater than a width of the scintillation crystal 112, causing the photodetector 304 to extend beyond the scintillation crystal 112 over part of an adjacent scintillation crystal 112. Since that part of the adjacent scintillation crystal 112 has a reflective coating 208, light from the adjacent scintillation crystal 112 will not be read by that photodetector 304. This allows some embodiments to have photodetectors 304 with active areas 308 with dimensions that are greater than the width of the scintillation crystal 112.

Figure 4:
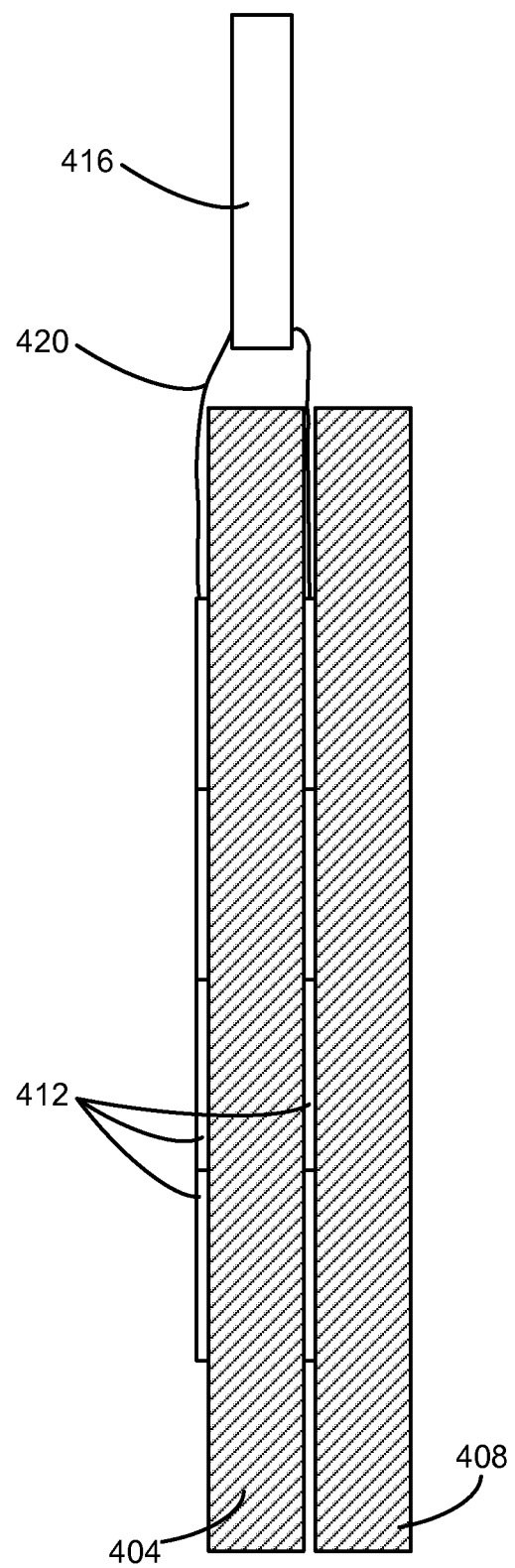
FIG. 4 is side view of a first row of scintillation crystals over a second row of scintillation crystals.

FIG. 4 is side view of a first row of scintillation crystals 404 over a second row of scintillation crystals 408. In this embodiment, the photodetectors 412 are over the rows of scintillation crystals 404, 408. The photodetectors 412 are connected to a circuit board 416 by wiring 420, such as flex circuit connectors. In an example, if the second row of scintillation crystals 408 have widths of 2.5 mm and the photodetectors 412 have thicknesses of 20μ, then the packing fraction, which is the area of the end of a scintillation crystal divided by the area of the end of a crystal and the area of an end of a photodetector, would be about 92%.

In operation, a high energy photon resulting from electron-positron annihilation enters a scintillation crystal 112 in the direction indicated by arrow 316. The scintillation crystal 112 causes the high energy photon to create lower energy photons, which are detected by the two photodetectors 304 paired with the scintillation crystal 112. The difference or ratio of intensities detected at the two photodetectors 304 and the time differences between detection may be used to determine time-of-flight and depth-of-interaction.

In this embodiment, where two discrete photodetectors 304 are provided for each scintillation crystal 112, the photodetectors 304 are capable of both depth-of-interaction and time-of-flight measurement. In this embodiment, the photodetectors 304 are solid state photomultipliers. These two photodetectors 304 read out light from the side of the scintillation crystal 112 which results in a very low transit time variance of the light photons from the scintillation interaction to absorption in the photodetector 304. Also, because of intensity and time differences in arrival time between the two photodetectors 304, a map between different depths can be recovered using the signal amplitude recorded from both photodetectors 304. In this way, both excellent time resolution and depth-of-interaction can be recovered. Secondly, because only at a minimum two discrete photodetectors 304 are used, another two discrete photodetectors 304 can be placed offset to the first. In this way, a larger photodetector 304 with dimensions and pitch of 4 mm can be used to read out a scintillation crystal 112 that is smaller all the way down to 2 mm. Also, another advantage of the side readout is the large aspect ratio and high surface area coverage of photodetector 304 on the scintillation crystal 112. When the scintillation crystal 112 is read out from the end of the scintillation crystal 112, it suffers from transit time variances, poor light collection efficiency, and poor surface area coverage of the sensor. Furthermore, because the detectors are placed directly on the side of the crystal, there is no need for complicated light guides to guide light to the active area of the device and avoid any dead areas. Since two photodetectors 304 per scintillation crystal 112 provide depth-of-interaction information, the scintillation crystals 112 may have a length of at least 8 mm. More preferably, the scintillation crystals 112 have a length of at least 10 mm.

Figure 5:
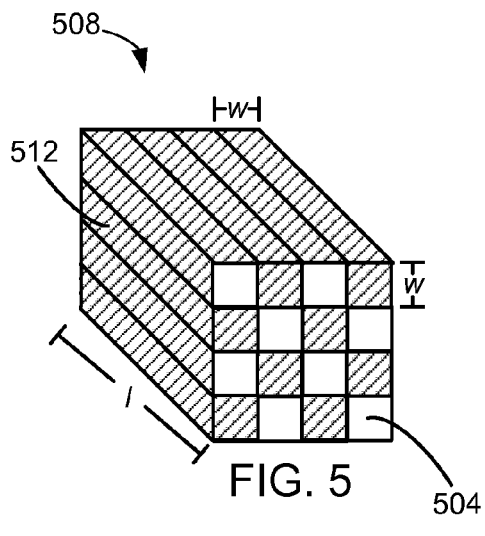
FIG. 5 is a perspective view of scintillation crystals placed adjacent to each other so that their lengths are parallel and so that they form a 4×4 matrix.

In another embodiment, FIG. 5 is a perspective view of scintillation crystals 504 placed adjacent to each other so that their lengths are parallel and so that they form a 4×4 matrix 508. A reflective coating 512 is placed on five sides of each scintillation crystal 504. One end of each scintillation crystal 504 does not have a reflective coating. The ends of the scintillation crystal 504 that do not have a reflective coating are ends where both dimensions of the end are widths of the scintillation crystal 504 shown by the dimension "w," and not the length shown by the dimension "l". In this embodiment, the widths "w" are equal providing square ends. In other embodiments, the widths "w" may not be equal, but are both less than the length "l." The ends of the scintillation crystals 504 that do not have a reflective coating are alternated so that adjacent scintillation crystals 504 in a matrix 508 have opposite ends that do not have reflective coatings, and scintillation crystals 504 that are diagonal within the matrix 508 have the same ends that do not have a reflective coating. This causes the reflective coating 512 at each end of the matrix 508 to form a grid of open spaces. More preferably, the reflective coating 512 at each end is a checkerboard, as shown.

Figure 6:
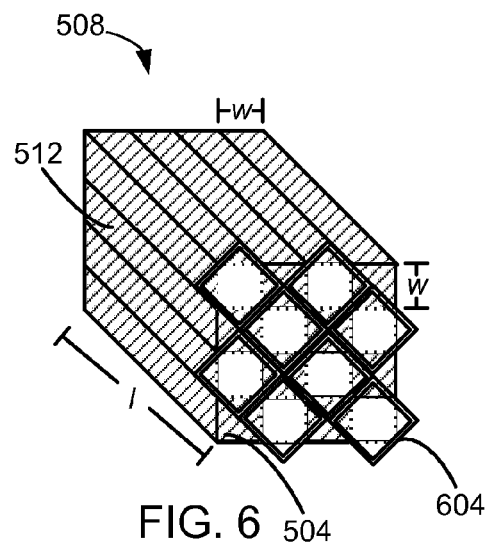
FIG. 6 is a perspective view of the 4×4 matrix of scintillation crystals with photodetectors placed over the ends that do not have a reflective coating.
Figure 7:
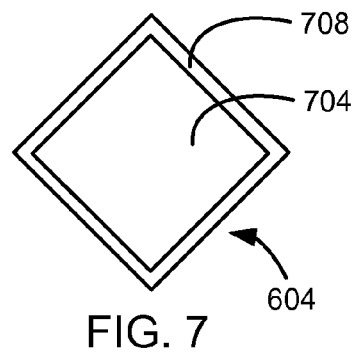
FIG. 7 is an enlarged view of one of the photodetectors.

FIG. 6 is a perspective view of the 4×4 matrix 508 of scintillation crystals 504 with photodetectors 604 placed over the ends that do not have a reflective coating. FIG. 7 is an enlarged view of one of the photodetectors 604. In this example, the photodetector 604 comprises an active area 704 surrounded by a dead area 708. The widths of the photodetectors 604 are a square root of 2, so that the photodetectors 604 are wider than the scintillation crystals 504.

Figure 8:
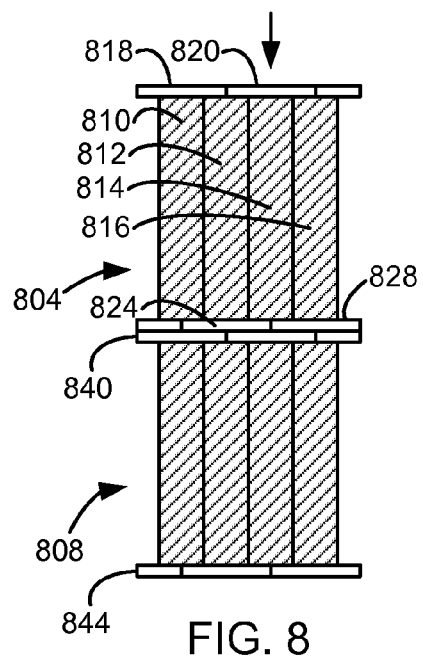
FIG. 8 is a side view of a first 4×4 matrix of scintillation crystals over a second 4×4 matrix of scintillation crystals.

FIG. 8 is a side view of a first 4×4 matrix of scintillation crystals 804 over a second 4×4 matrix of scintillation crystals 808. In the first 414 matrix of scintillation crystals 804, scintillation crystals 810 and 814 are read by photodetectors 818 and 820, respectively, on a first side of the first 4×4 matrix of scintillation crystals 804, and scintillation crystals 812 and 816 are read by photodetectors 824 and 828, respectively, on a second side of the first 4×4 matrix of scintillation crystals 804. As shown, alternating scintillation crystals are read by photodetectors on opposite sides of the matrix which allows for the reflective coating with a grid of open spaces, preferably a checkerboard pattern, to allow for the oversized diagonal photodetectors 604, which need to only receive data from every other scintillation crystal 504. By using photodetectors 604 with widths equal to a square root of 2, and rotating the photodetectors 604 45° with respect to the ends of the scintillation crystals 504, only a small part of the dead area 708 is coupled to a scintillation crystal 504, which minimizes the effect of the dead area 708.

The second 4×4 matrix of scintillation crystals 808 also has photodetectors 840 on a first side and photodetectors 844 on a second side, so that photodetectors 840 on one side only detect photons from alternating scintillation crystals. The shorter scintillation crystals 504 in this embodiment of the invention have significantly reduced transit time variance, and higher light collection efficiency. The stacked first 4×4 matrix of scintillation crystals 804 and second 4×4 matrix of scintillation crystals 808 provide discrete depth-of-interaction capability to the detector.

The actual detectors may have any N×M array of scintillation crystals. For this embodiment, the packing fraction would be about 100%. As in the previous embodiment, the photodetectors are electrically connected to a circuit board or readout device, such as a computer system.

Figure 9:
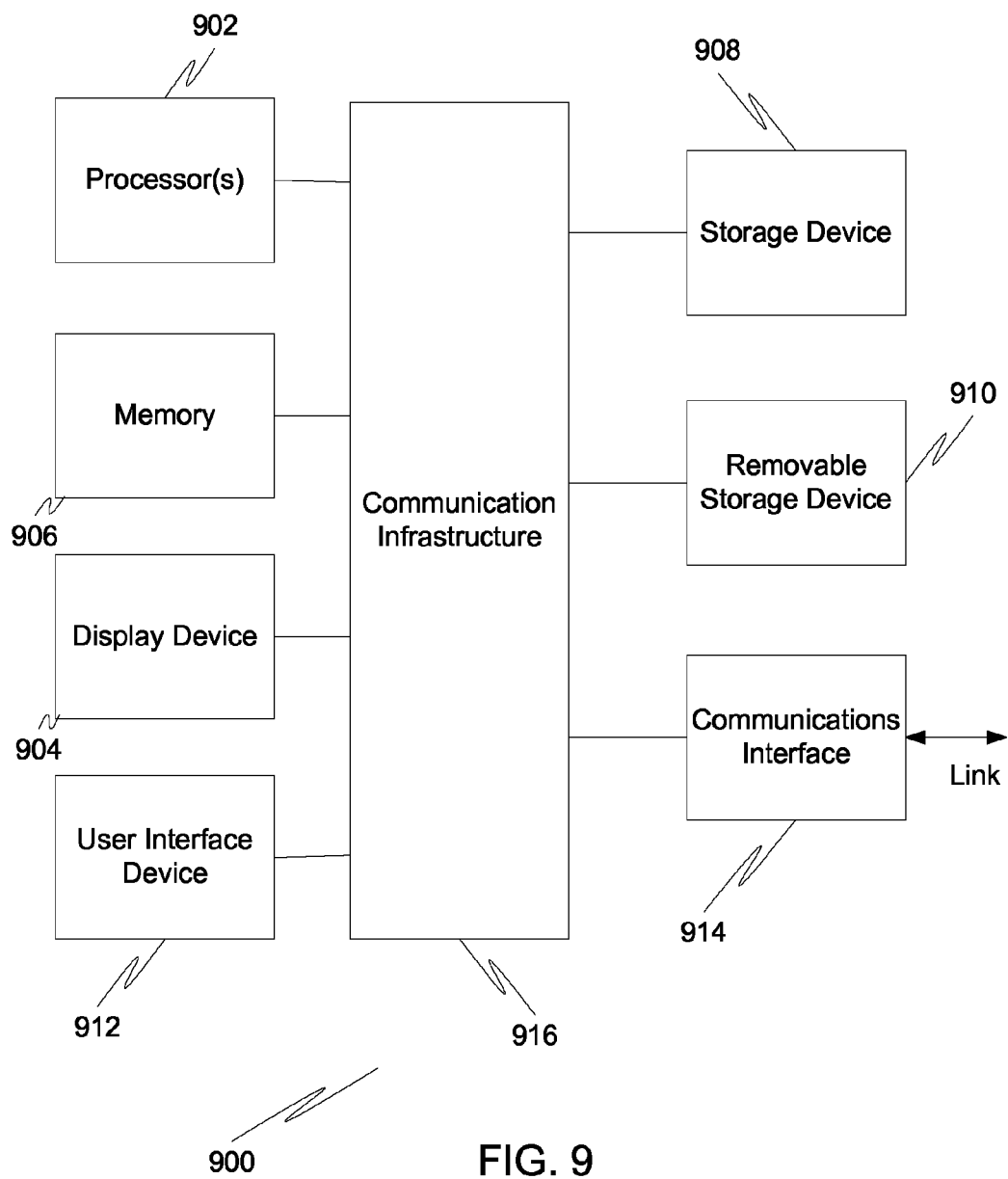
FIG. 9 is a high level block diagram showing a computer system, to which the photodetectors may be attached.

FIG. 9 is a high level block diagram showing a computer system 900, to which the photodetectors may be attached. The computer system may have many physical forms ranging from an integrated circuit, a printed circuit board, and a small handheld device up to a huge super computer. The computer system 900 includes one or more processors 902, and further can include an electronic display device 904 (for displaying graphics, text, and other data), a main memory 906 (e.g., random access memory (RAM)), storage device 908 (e.g., hard disk drive), removable storage device 910 (e.g., optical disk drive), user interface devices 912 (e.g., keyboards, touch screens, keypads, mice or other pointing devices, etc.), and a communication interface 914 (e.g., wireless network interface). The communication interface 914 allows software and data to be transferred between the computer system 900 and external devices via a link. The system may also include a communications infrastructure 916 (e.g., a communications bus, cross-over bar, or network) to which the aforementioned devices/modules are connected.

Information transferred via communications interface 914 may be in the form of signals such as electronic, electromagnetic, optical, or other signals capable of being received by communications interface 914, via a communication link that carries signals and may be implemented using wire or cable, fiber optics, a phone line, a cellular phone link, a radio frequency link, and/or other communication channels. With such a communications interface, it is contemplated that the one or more processors 902 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

The computer system 900 receives data from the photodetectors and uses the data to perform a reconstruction to create a three dimensional image, which the computer system 900 displays. These embodiments provide a system that has a readout of not more than 200 ps. In another embodiment, such systems are able to provide a time-of-flight resolution of less than 300 ps when using lutetium oxyorthosilicate (LSO) or lutetium-yttrium oxyorthosilicate (LYSO) scintillation crystals.

Shielding

Figure 10:
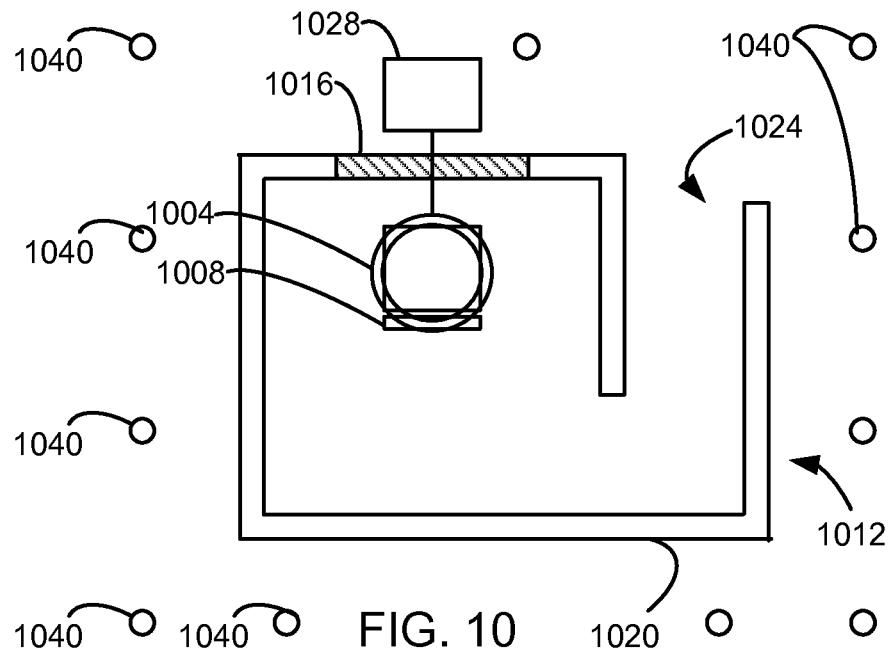
FIG. 10 is a top view of a self-shielded PET comprising a PET scanner with a chair, surrounded by a shielding system.

FIG. 10 is a top view of a self-shielded PET comprising a PET scanner 1004 with a chair 1008, surrounded by a shielding system 1012. The shielding system 1012 comprises an optically transparent high energy photon shield 1016 adjacent to the PET scanner 1004 and a high energy photon shield 1020, so that the optically transparent high energy photon shield 1016 and the high energy photon shield 1020 surround the PET scanner 1004. In this embodiment, the PET scanner 1004 uses a clam shell ring that is able to split and open to allow the patient to enter the ring 1020 while sitting or standing. In this embodiment, the high energy photon shield forms a gap 1024, which allows a patient to enter the shielding system 1012 to have access to the PET scanner 1004 and to sit on the chair 1008. A computer system 1028 is connected to the PET scanner 1004. The computer system 1028 may be used to control the PET scanner 1004 and process data from the PET scanner 1004. A technician operates the computer system 1028 in an area protected from high energy photons and is able to view the patient through the optically transparent high energy photon shield 1012. In one embodiment, a plurality of columns 1040 is place around the shielding system 1012.

Figure 11:
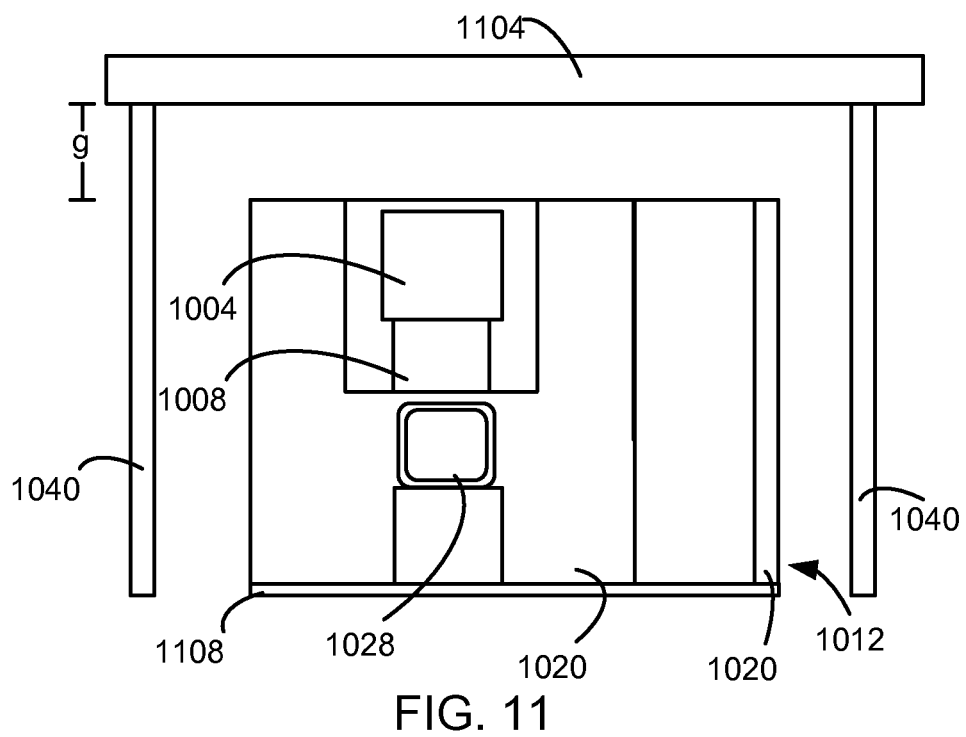
FIG. 11 is a front view of the shielding system.

FIG. 11 is a front view of the shielding system 1012, comprising the optically transparent high energy photon shield 1016 and the high energy photon shield 1020. The optically transparent high energy photon shield 1016 is adjacent to the PET scanner 1004 and chair 1008. The computer system 1028 is connected to the PET scanner 1004. A high energy photon shield roof 1104 is provided above the shielding system 1012, and is supported by the plurality of columns 1040. A gap "g" of at least one foot is between the top of the shielding system 1012 and the high energy photon shield roof 1104. For example, the shielding system 1012 is no more than 7 feet tall, for example 6 feet 6 inches, and the high energy photon shield roof is at least 8 feet high, for example 8 feet high. In other embodiments, the shielding system 1012 may contact the high energy photon shield roof 1104, however preferably, there is a gap of at least one foot between the high energy photon shield roof 1104 and the shielding system 1012 for at least a third of the length of the high energy photon shield 1020. If a room is below the shielding system 1012, a floor shielding system 1108 may be attached to the bottom of the shielding system 1012.

A major problem with the current solution in shielding the radiation emitted from patients undergoing PET scans is that it is incorporated into the room of the patient. Because the shielding is far away from the source of the radiation, it has to cover a very large area of the walls of the room: roof, side walls and floor. This is especially true in places where the depth-of-interaction scanner is placed on the second or higher floor of a multi-story hospital or imaging center. This shielding must be made of heavy dense materials such as lead. Because of the excessive weight of the lead, it may be the case that the room must be seismically retrofitted to support the added weight of the lead. This can lead to substantial costs that rival the cost of the depth-of-interaction scanner itself. For a dedicated system, because the footprint and cost of the camera is much lower, there is a desire to significantly reduce this installation cost of the system.

In a non-limiting example, the optically transparent high energy photon shield 1016 is leaded x-ray glass that is made thick enough to stop some fraction of the high energy annihilation photons at 511 keV energy. Although the optically transparent high energy photon shield 1016 does not completely enclose the patient, it has less of a claustrophobic effect and allows a technician to view the patient. In addition, the gap "g" between the shielding system 1012 and the high energy photon shield roof 1104 further reduces claustrophobic effects of being placed in the depth-of-interaction scanner, while providing high energy photon protection.

Figure 12A:
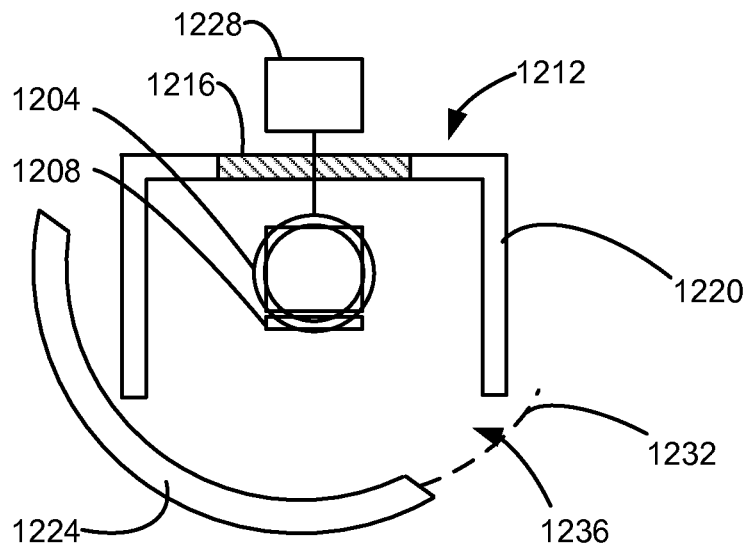
FIG. 12A is a top view of another embodiment of a self-shielded PET.

FIG. 12A is a top view of another embodiment of a self-shielded PET comprising a PET scanner 1204 with a chair 1208, surrounded by a shielding system 1212. The shielding system 1212 comprises an optically transparent high energy photon shield 1216 adjacent to the PET scanner 1204 and a high energy photon shield 1220, so that the optically transparent high energy photon shield 1216 and the high energy photon shield 1220 surround the PET scanner 1204. A computer system 1228 is connected to the PET scanner 1204. Part of the high energy photon shield 1220 is a door 1224. In this embodiment, the door 1224 is in the shape of part of a circle and slides on a track 1232 that forms part of a circle to provide an opening 1236, as shown.

Figure 12B:
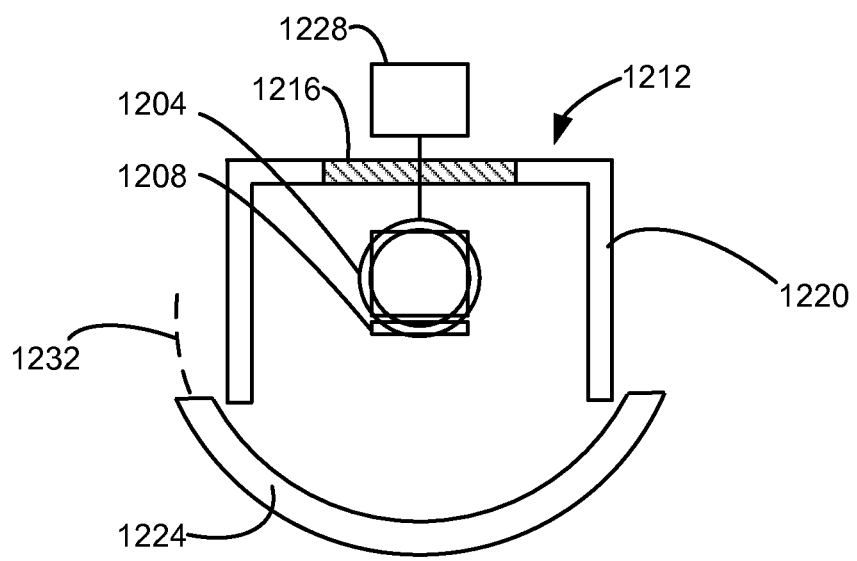
FIG. 12B is a top view of the embodiment shown in FIG. 12A after the door has been slid on the track to close the shielding system.

FIG. 12B is a top view of the embodiment shown in FIG. 12A after the door 1224 has been slid on the track 1232 to close the shielding system 1212. In this embodiment, the door 1224 is manually opened and closed, without the use of a motor. In addition, a gap may be between the door 1224 and the remaining shielding system 1212 to prevent pinching or injury if a person is between the door 1224 and the remaining shielding system 1212.

In these embodiments, the patient would sit on the chair 1208. By sitting the patient in the chair 1208, the patient has a smaller footprint than in a scan that requires a patient to lie down. The smaller PET footprint, allows for the more compact shielding described in the embodiments. PET provides high energy photons which require more shielding than most other medical imaging devices. The higher shielding requires increased weight for the shielding. In these embodiments, a self-shield dedicated scanner can be built that has significant less weight, and therefore, lower installation costs than tradition PET scanners that shield an entire room, requiring extensive room shielding, and potential seismic upgrades.

Limited Angle Panels

Limited angle tomography systems provide a cost effective means of measuring a limited field-of-view without requiring a large ring system. Such limited angle tomography systems are described in US Patent Application Publication US 2010/0108896 to Surti et al. entitled "Limited Angle Tomography with Time-Of-Flight PET," which is incorporated by reference for all purposes.

In this invention, the parameters that determine relative size of the panels are specified to focus on a field-of-view that is offset from the center. Non-limiting examples of these applications can be head and neck cancer or cardiac imaging. In the case of head and neck cancer, the mouth is offset from the central axis of the patient. In the case of cardiac imaging, the heart is offset above the central axis of the patient. In these applications, it can be desirable to minimize the width of the panels, while at the same time, maximizing the sensitivity of the system to an offset field of view. By changing the relative size of the panels, better angular coverage can be achieved for a field-of-view that is offset from the central axis. The panels can be curved or they can be flat. There is an advantage if the panels are curved. When the panels are curved, they have a higher sensitivity, and less depth-of-interaction blurring than when the panels are flat. Besides the width of the panels, there are several parameters that are optimized to optimally build a offset field of view scanner, such as the axial extent of the depth-of-interaction scanner, which determines the field-of-view in the axis perpendicular to the offset field-of-view, the total amount of detector material that stops the photons, which defines the intrinsic sensitivity of the detector panel, the spatial and time resolution of the detector panel, which determines the reconstructed resolution, the angular coverage, which is calculated from the distance between the panels, and the width of each of the panels, which determine which angles an object placed between them samples.

Figure 13:
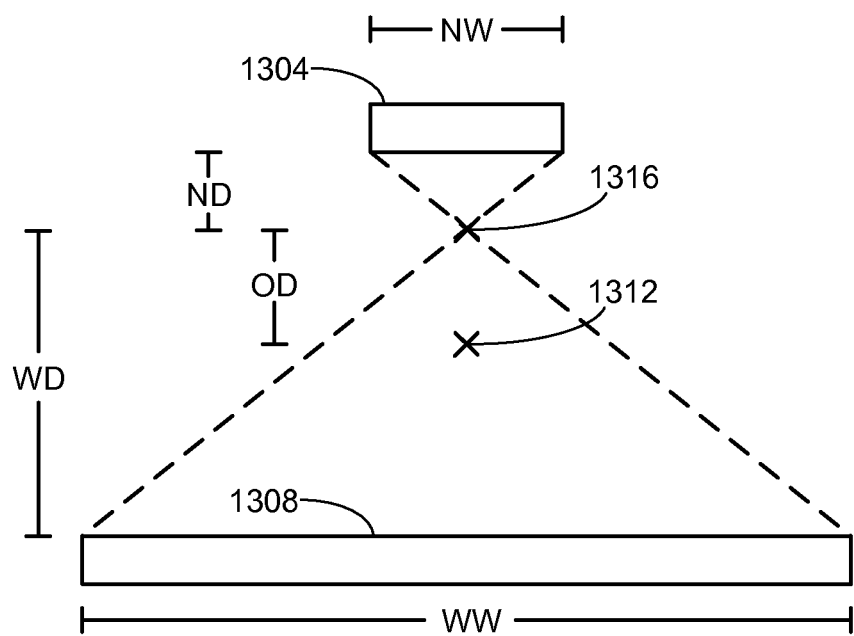
FIG. 13 is a schematic view of a limited angle tomography system.

In another embodiment, the size of the detector panels is optimized when imaging an object offset by a fixed distance from the center of the panels. FIG. 13 is a schematic view of a limited angle tomography system, using a narrower panel 1304 and a wider panel 1308, where the narrower panel 1304 has a width less than half the width of the wider panel 1308. The difference in widths of the panels allows for the focusing on an object offset from the center 1312 of the panels 1304, 1308, defined as a point equal distant from at least two points from the narrower panel 1304 and two points from wider pane 1308. The width of the narrower panel 1304 is NW. The width of the wider panel 1308 is WW. The distance from the narrower panel 1304 to the center 1312 is ND. The distance from the wider panel 1308 to the center 1312 is WD. An offset distance between a focus point 1316 and the center 1312 is OD. The offset distance may be calculated by the equation 2 (WW+NW).

Figure 14:
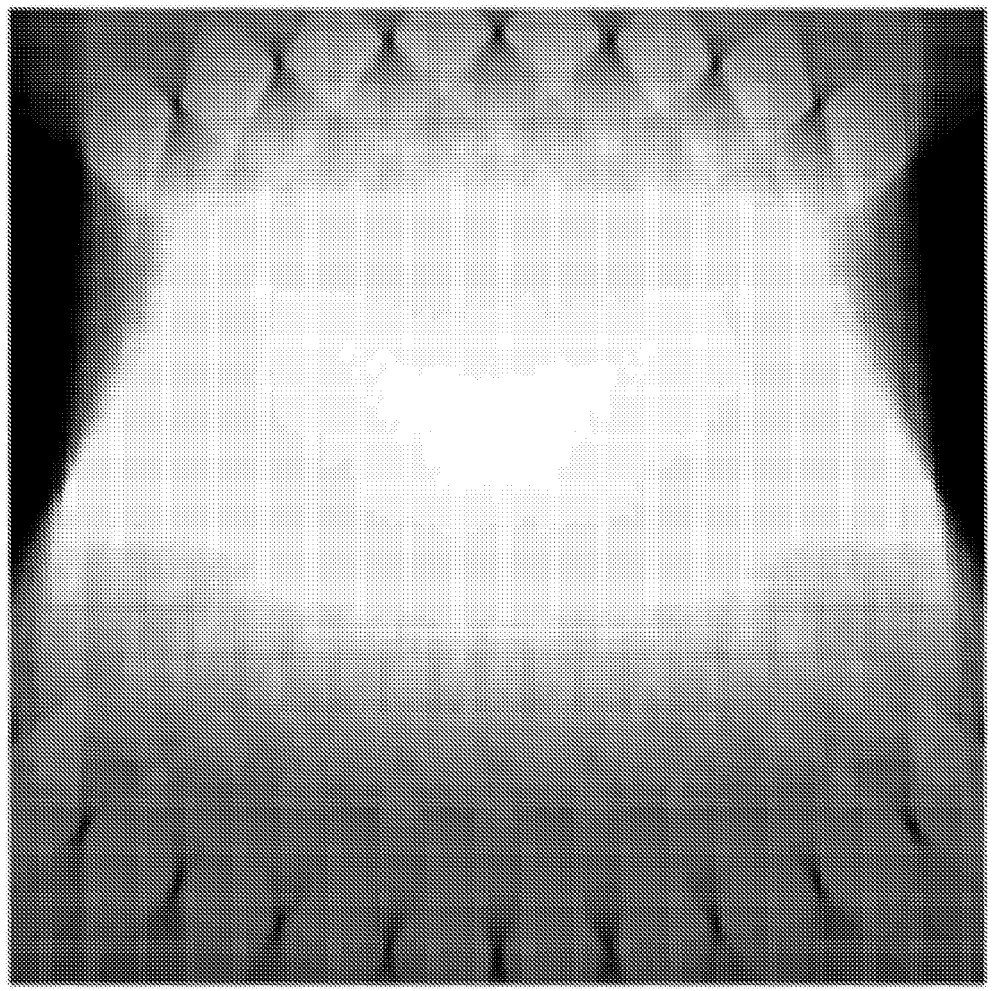
FIG. 14 is a calculated sensitivity map of a system built according to the schematic shown in FIG. 13.

FIG. 14 is a calculated sensitivity map of a system built according to the schematic shown in FIG. 13. The peak of the sensitivity, the focus point, is clearly shifted above the central axis of the depth-of-interaction scanner. In embodiments using curved panels, the arc length of each panel may be used as the panel width.

Because the depth-of-interaction scanner uses time-of-flight information, the sizes of the detector panels can be further reduced to minimize cost of the depth-of-interaction scanner. Even for limited-angle time-of-flight PET systems, the focusing method still works.

Including time-of-flight information, some embodiments incorporate the use of depth-of-interaction information. Because of the length of the crystal, adding depth-of-interaction improves the time-of-flight localization, but in limited angle tomography, it also improves the angular sampling. Finally, in embodiments where this limited angle tomography systems will be used, it will likely be placed close to the patient to maximize sensitivity. When detector panels are placed close to the patient, there is a depth-of-interaction blurring of the event. By adding depth-of-interaction information, these embodiments minimize depth of penetration blurring effects.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A detector comprising:
    a plurality of scintillation crystals, where each scintillation crystal of the plurality of scintillation crystals has a width, and wherein each scintillation crystal of the plurality of scintillation crystals is placed adjacent to each other so that first surfaces of the plurality of scintillation crystals form a first rectangular surface; and
    a reflective coating over the first rectangular surface with an open region grid pattern, wherein each open region forms a space wherein each space has a width equal to the width of a scintillation crystal of the plurality of scintillation crystals; and
    a plurality of photodetectors wherein each photodetector of the plurality of photodetectors is placed over a space, wherein the photodetector has a width greater than the width of the space over which the photodetector is placed; and
    at least one electronic readout electrically connected to the plurality photodetectors.

2. The detector, as recited in claim 1, wherein each scintillation crystal of the plurality of scintillation crystals is rectangular prisms.

3. The detector, as recited in claim 2, wherein each photodetector is a solid state photomultiplier.

4. The detector, as recited in claim 3, wherein the at least one electronic readout has a time-of-flight time resolution of less than 300 ps when using a LSO or LYSO scintillation crystal.

5. The detector, as recited in 4, wherein each scintillation crystal of the plurality of scintillation crystals has a length of at least 8 mm.

6. The detector, as recited in claim 5, wherein each scintillation crystal of the plurality of scintillation crystals has a first photodetector of the plurality of photodetectors and a second photodetector of the plurality of photodetectors.

7. The detector, as recited in claim 1, wherein the plurality of scintillation crystals are used in a positron emission tomography (PET) scanner, further comprising a processor that receives said emission signals from the at least one electronic readout of the plurality photodetectors and processes said signals into a three dimensional reconstruction.

8. The detector, as recited in claim 1, wherein each photodetector is a solid state photomultiplier.

9. The detector, as recited in claim 1, wherein the at least one electronic readout has a time-of-flight time resolution of less than 300 ps when using a LSO or LYSO scintillation crystal.

10. The detector, as recited in 1, wherein each scintillation crystal of the plurality of scintillation crystals has a length of at least 8 mm.

11. The detector, as recited in claim 1, wherein each scintillation crystal of the plurality of scintillation crystals has a first photodetector of the plurality of photodetectors and a second photodetector of the plurality of photodetectors.

12. The detector, as recited in claim 11, further comprising a processor for depth-of-interaction determination using signal amplitude recorded from both the first photodetector and second photodetector.

13. The detector, as recited in claim 1, wherein each photodetector of the plurality of photodetectors has a width that is equal to the square root of two times with width of the scintillation crystals.

14. The detector, as recited in claim 13, where each photodetector of the plurality of photodetectors is adjacent to an end of a scintillation crystal.

* * * * *